(12) United States Patent
Okamoto et al.

(10) Patent No.: US 8,940,934 B2
(45) Date of Patent: Jan. 27, 2015

(54) PRODUCTION PROCESS OF α-HYDROXY ACIDS

(75) Inventors: Makoto Okamoto, Tokyo (JP); Hideki Date, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 295 days.

(21) Appl. No.: 12/999,785

(22) PCT Filed: Jun. 20, 2008

(86) PCT No.: PCT/JP2008/061365
§ 371 (c)(1),
(2), (4) Date: Dec. 17, 2010

(87) PCT Pub. No.: WO2009/153886
PCT Pub. Date: Dec. 23, 2009

(65) Prior Publication Data
US 2011/0098438 A1    Apr. 28, 2011

(51) Int. Cl.
C07C 51/42 (2006.01)
C08G 63/08 (2006.01)
C07C 51/02 (2006.01)
C07C 51/41 (2006.01)
C07D 319/12 (2006.01)
C12P 7/42 (2006.01)

(52) U.S. Cl.
CPC .............. C08G 63/08 (2013.01); C07C 51/02 (2013.01); C07C 51/412 (2013.01); C07D 319/12 (2013.01); C12P 7/42 (2013.01)
USPC ........... 562/593; 435/129; 435/136; 435/139; 528/354; 528/361; 549/274; 562/588; 562/589; 562/590

(58) Field of Classification Search
USPC .................. 435/129, 136, 139; 528/354, 361; 549/274; 562/513, 588, 589, 590, 593
See application file for complete search history.

(56) References Cited

U.S. PATENT DOCUMENTS

| 3,622,455 A * | 11/1971 | Iizuka et al. ................. 435/144 |
|---|---|---|
| 3,799,980 A * | 3/1974 | Nara et al. .................... 562/580 |
| 5,814,498 A | 9/1998 | Mani et al. |
| 5,830,991 A | 11/1998 | Shiiki et al. |
| 5,932,454 A | 8/1999 | Matsuoka et al. |
| 2003/0158360 A1 * | 8/2003 | Gerking et al. ............ 526/317.1 |
| 2004/0087805 A1 | 5/2004 | Yamane et al. |
| 2004/0210087 A1 | 10/2004 | Meng et al. |
| 2005/0070738 A1 | 3/2005 | Isotani |
| 2009/0118541 A1 | 5/2009 | Hinago et al. |

FOREIGN PATENT DOCUMENTS

| BE | 1009874 | * 10/1997 |
|---|---|---|
| EP | 0 884 300 | 12/1998 |
| JP | 62-023823 | 1/1987 |
| JP | 63-2596 | 1/1988 |
| JP | 63-209592 | 8/1988 |
| JP | H04197424 A | 7/1992 |
| JP | 6-303991 | 11/1994 |
| JP | 9-328481 | 12/1997 |
| JP | 10-179183 | 7/1998 |
| JP | 11-075885 | 3/1999 |
| JP | 11-180971 | 7/1999 |
| JP | 2000-119214 | 4/2000 |
| JP | 2001-299378 | 10/2001 |
| JP | 2004-196768 | 7/2004 |
| JP | 2004-519485 | 7/2004 |
| JP | 2004-532855 | 10/2004 |
| JP | 2005-132836 | 5/2005 |
| JP | 2007-295820 | 11/2007 |
| WO | 97/30962 | 8/1997 |
| WO | 99/00350 | 1/1999 |
| WO | 00/59847 | 10/2000 |
| WO | 2006/069114 A2 | 6/2006 |
| WO | 2006/126626 A1 | 11/2006 |

OTHER PUBLICATIONS

Japanese Office Action for corresponding Japanese Application No. 2006-348270 dated Jan. 31, 2012 with partial English translation.

* cited by examiner

*Primary Examiner* — Gregory Listvoyb
(74) *Attorney, Agent, or Firm* — Morgan, Lewis & Bockius LLP

(57) ABSTRACT

An object of the present invention is to provide a production process of an α-hydroxy acid having a sufficient quality as a polymer raw material, which process does not produce a large amount of waste as a byproduct and is economical.

The present invention provides a production process of an α-hydroxy acid having a step of adding a basic metal to an α-hydroxy acid ammonium salt to yield an α-hydroxy acid metal salt and a step of desalting the α-hydroxy acid metal salt to yield the α-hydroxy acid.

23 Claims, 2 Drawing Sheets

PRODUCTION PROCESS OF α-HYDROXY ACIDS

RELATED APPLICATIONS

The present application is a U.S. National Phase Application of International Application No. PCT/JP2008/061365 (filed Jun. 20, 2008) which is hereby incorporated by reference in their entirety.

TECHNICAL FIELD

The present invention relates to a practical industrial process for producing α-hydroxy acids from α-hydroxy acid ammonium salts, in particular, to a process for producing α-hydroxy acids from α-hydroxy acid ammonium salts obtained by the hydrolysis of α-hydroxynitriles. The α-hydroxy acids obtainable by the present process have a desirable quality as a raw material for producing the corresponding poly-α-hydroxy acids.

BACKGROUND ART

Poly-α-hydroxy acids are biodegradable polymers and they are hydrolyzed in vivo. In natural environments, they are metabolized/decomposed into water and a carbon dioxide gas with an aid of microorganisms. In recent days, poly-α-hydroxy acids have therefore drawn attentions as eco-friendly polymer materials. Of these, polylactic acid and polyglycolic acid have drawn attentions as eco-friendly polymer materials to be used instead of medical materials or general-purpose resins. In particular, polyglycolic acid has attracted attentions as a polymer material to be used for gas barrier applications due to its typical properties, that is, gas barrier properties.

Since it is difficult to obtain a high-molecular-weight poly-α-hydroxy acid directly by dehydration condensation of an α-hydroxy acid, a process for obtaining a high-molecular-weight poly-α-hydroxy acid by preparing a cyclic dimer ester first and then carrying out ring-opening polymerization is known. In the case of the production of, for example, polylactic acid or polyglycolic acid, it is known to produce it by synthesizing lactide or glycolide which is a cyclic dimer ester and then subjecting the lactide or glycolide to ring-opening polymerization in the presence of a catalyst. It is however necessary to use high-purity lactide or glycolide in order to obtain high-molecular-weight polylactic acid or polyglycolic acid by ring-opening polymerization of lactide or glycolide. As a process for obtaining high-purity lactide or glycolide from lactic acid or glycolic acid, there is disclosed a process for synthesizing a lactic acid or glycolic acid oligomer and then depolymerizing it in a polar organic solvent having a high boiling point (Patent Document 1).

In the process for depolymerizing a glycolic acid oligomer to prepare glycolide, a trace amount of alkali metal ions contained in the oligomer becomes a cause for destabilizing the depolymerization reaction system, but long-term stability of the depolymerization reaction can be achieved by adding, to the reaction system, a sulfate salt or organic acid salt of divalent or higher-valent cations even in the presence of the alkali metal ions (Patent Document 2).

Thus, α-hydroxy acids which will serve as raw materials of the corresponding poly-α-hydroxy acids are obtainable by converting α-hydroxy acid ammonium salts into the corresponding α-hydroxy acids.

As the most common process for converting carboxylic acid ammonium salts into the corresponding carboxylic acids, a process of adding a strong acid such as sulfuric acid to the salts, thereby obtaining both free acids and by-product ammonium sulfate can be given. A process of producing a large amount of waste products such as ammonium sulfate is however undesirable from an environmental standpoint.

As a process for converting carboxylic acid ammonium salts into the corresponding carboxylic acids, there are disclosed a process of producing an α-hydroxycarboxylic acid by thermally hydrolyzing its ammonium salt, and taking, out of the system, both an inert gas and an ammonia gas which is a product, thereby shifting equilibrium to the side of the reaction product obtained by thermal hydrolysis (Patent Document 3) and a process of producing 2-hydroxy-4-methylthiobutanoic acid from ammonium 2-hydroxy-4-methylthiobutanoate by heating it under pressure, thereby accelerating a shift of equilibrium to the side of the reaction product of thermal hydrolysis and evaporating ammonia with water (Patent Document 4).

Thermal hydrolysis of an ammonium carboxylate needs, however, a great deal of energy and in addition, it takes much time to carry out 100% conversion into its free acid so that thermal hydrolysis is not a practical process. When ammonia is removed from an ammonium carboxylate only by thermal hydrolysis, energy enough for separating the bond between carboxylate anions and ammonium cations is required. As the amount of ammonium cations gets smaller, the energy necessary for separation increases, which makes the separation more difficult. Moreover, heat treatment of an ammonium carboxylate produces the corresponding carboxylic acid amide, which leads to a serious problem in consideration of the quality of the final product.

Not a simple thermal hydrolysis but a process using some sort of a reactant is therefore proposed. For example, there is disclosed a process of reacting ammonium succinate with an alcohol or water to eliminate ammonia and obtaining succinic acid or a derivative thereof while collecting the ammonia thus eliminated (Patent Document 5). The reaction with an alcohol however produces a succinate ester, which requires hydrolysis again and therefore complicates the preparation step.

There is also disclosed a process of heating and decomposing ammonium lactate in the presence of an organic amine which is immiscible in water and preparing a reaction product containing lactic acid and the organic amine (Patent Document 6). Although this process can certainly remove ammonia from the ammonium salt, further purification is necessary for obtaining a high-purity free acid from the resulting mixture with the organic amine. Accordingly, it can be expected easily that it may complicate the preparation step.

There is also disclosed a process of producing α-hydroxy-4-methylthiobutyric acid by heating ammonium α-hydroxy-4-methylthiobutyrate, which has been obtained by biologically hydrolyzing α-hydroxy-4-methylthiobutyronitrile and then concentrating the hydrolysate, in an ether solvent having two or more ether bonds and distilling off the thus-liberated ammonia (Patent Document 7). Although this process enables removal of ammonia from the ammonium salt to reduce the residual ratio of ammonia to about 0.12%, this process produces a carboxylic acid, which leads to a serious problem in consideration of the quality of the final product.

There is also proposed a process of removing ammonia by utilizing a dehydration condensation reaction of a hydroxycarboxylic acid itself without adding an extraneous reactant. For example, there is disclosed a process comprising a first step of heating ammonium α-hydroxy-4-methylthiobutyrate to convert it into a low-molecular-weight poly-α-hydroxy-4-methylthiobutyric acid while removing water and ammonia and a second step of adding water to it and heating the resulting mixture to hydrolyze the low-molecular-weight polymer into the corresponding free acid (Patent Document 8). Production of the amide as a by-product in the first step is, however, inevitable and a portion of it becomes ammonium α-hydroxy-4-methylthiobutyrate as a result of the hydrolysis in the second step. Ammonia cannot therefore be removed enough to raise the purity. In addition, the conversion ratio by the hydrolysis reaction in the second step does not reach 100% and a portion of the low-molecular-weight poly-α-hydroxy-4-methylthiobutyric acid remains and poses a quality problem. In fact, Patent Document 8 describes therein that the purity is approximately 80% and purification such as extraction is necessary to obtain an α-hydroxy acid with a higher purity.

A process using an ion exchange resin is also proposed. There is disclosed, for example, a process of obtaining a carboxylic acid by adsorbing ammonium cations of an aqueous solution of ammonium methacrylate to a cation exchange resin and collecting the ammonium cations thus adsorbed to the resin as ammonia by using an organic solvent (Patent Document 9). The ammonia decomposition ratio does not reach a satisfactory level and therefore this process is far from an industrially usable process.

As a further process, there is also disclosed a process of collecting a carboxylic acid and ammonia from the corresponding ammonium carboxylate by electrodialysis using a system composed of a bipolar membrane, an anion membrane, and a bipolar membrane (Patent Document 10). If a carboxylic acid amide is contained as an impurity, however, it prevents purification using electrodialysis or even if it does not prevent the purification, the carboxylic acid amide accumulates in a recycled liquid.

Moreover, there is proposed a process of obtaining, from an ammonium salt of a carboxylic acid such as dicarboxylic acid, tricarboxylic acid or amino acid, the free acid by reaction crystallization using a volatile carboxylic acid having a lower ionization exponent than that of the above-described carboxylic acid and collecting the volatile acid from an ammonium salt of the volatile acid contained in the mother liquor (Patent Document 11). It is however difficult to completely remove the ammonia in the crystals of the free acid thus obtained. An inevitable residue of from about 2 to 3% of the ammonia poses a quality problem.

An α-hydroxy acid ammonium salt can be synthesized, for example, from an α-hydroxynitrile compound. Synthesis of a carboxylic acid compound from the α-hydroxynitrile compound can be performed using a biocatalyst having nitrile hydrolysis activity. Examples of the biocatalyst having nitrile hydrolysis activity and capable of converting a nitrile compound into a carboxylic acid compound include nitrilase and combination of nitrile hydratase and amidase.

The above-described process is advantageous because a reaction process can be simplified due to mild reaction conditions and a high-purity reaction product containing a relatively small amount of by-products can be prepared. Use of it for the preparation of various carboxylic acid compounds has therefore been investigated in recent years. Although the amount of by-products is not so much, impurities, for example, nitriles such as α-aminonitrile and iminodialkylnitrile, and amides or carboxylic acids which are hydrolysates thereof are produced by the hydrolysis of α-hydroxynitrile compounds.

The product obtained by the reaction is an ammonium carboxylate irrespective of the kind of the biocatalyst so that the ammonium carboxylate must be converted into the corresponding carboxylic acid by the above-described method. Also in this step, impurities such as α-hydroxy acid amide remain.

As an example utilizing a nitrile compound, there is proposed a process of producing a calcium α-hydroxycarboxylate from an ammonium α-hydroxycarboxylate which has been prepared from an α-hydroxynitrile by using a biocatalyst. Described specifically, there is disclosed a process of producing calcium 2-hydroxy-4-methylthiobutanoate by bringing a calcium source into contact with ammonium 2-hydroxy-4-methylthiobutanoate obtainable by the biological hydrolysis of 2-hydroxy-4-methylthiobutylonitrile (Patent Document 12). This Document however supposes the use of calcium 2-hydroxy-4-methylthiobutanoate as is as a feed additive and does not disclose the production of 2-hydroxy-4-methylthiobutanoic acid by desalting the calcium 2-hydroxy-4-methylthiobutanoate or production of a poly-α-hydroxy acid using 2-hydroxy-4-methylthiobutanoic acid as a raw material. Accordingly, as a matter of fact, it mentions neither the influence of impurities in an α-hydroxy acid on the preparation of the corresponding poly-α-hydroxy acid nor conditions for obtaining an α-hydroxy acid most suited as a polymer raw material.

There is also disclosed a process of reacting an α-hydroxynitrile with a microorganism having a nitrile hydrating capacity or a processed product thereof to yield the corresponding α-hydroxy acid amide and/or α-hydroxy acid ammonium salt, hydrolyzing the α-hydroxy acid amide in the presence of a base while subjecting the α-hydroxy acid ammonium salt to salt exchange, thereby producing the corresponding salt of the α-hydroxy acid, and carrying out, after removal of ammonia, electrodialysis to prepare the α-hydroxy acid and base (Patent Document 13). This document describes, in Examples, only a production example of 2-hydroxy-4-methylthiobutanoic acid to be used as is for animal feed or the like. It never describes the production of a poly-α-hydroxy acid from calcium 2-hydroxy-4-methylthiobutanoate. There is therefore no description on the conditions for obtaining the most suited α-hydroxy acid as a polymer raw material.

Even if the process disclosed in Patent Document 12 or 13 is employed, it is just conceivable that impurities, for example, nitriles such as α-aminonitrile and iminodialkylnitrile which are presumed to be by-products of the hydrolysis of an α-hydroxy acid amide or α-hydroxynitrile, or amides or carboxylic acids which are hydrolysates of the nitriles may remain in a final product of an α-hydroxy acid. These impurities have a serious influence on the quality of the α-hydroxy acid to be used as a polymer raw material but these documents do not describe the conditions permitting sufficient removal of these impurities.

[Patent Document 1] Japanese Patent Laid-Open No. Hei 9-328481
[Patent Document 2] Japanese Patent Laid-Open No. 2004-519485
[Patent Document 3] WO200059847 A1
[Patent Document 4] Japanese Patent Laid-Open No. 2000-119214
[Patent Document 5] Japanese Patent Laid-Open No. 2005-132836
[Patent Document 6] Japanese Patent Laid-Open No. 2004-532855
[Patent Document 7] WO199900350 A1
[Patent Document 8] WO199730962 A1
[Patent Document 9] Japanese Patent Laid-Open No. Sho 62-23823
[Patent Document 10] U.S. Pat. No. 581,449 A1
[Patent Document 11] Japanese Patent Laid-Open No. 2004-196768

[Patent Document 12] Japanese Patent Laid-Open No. Hei 11-75885

[Patent Document 13] Japanese Patent Laid-Open No. 10-179183

DISCLOSURE OF THE INVENTION

Problems to be Solved by the Invention

An object of the present invention is therefore to provide a process for producing an α-hydroxy acid having a sufficient quality as a polymer raw material which process does not produce a large amount of waste products and is economical. More specifically, the object of the present invention is to provide an industrial process for producing an α-hydroxy acid ideal as a raw material for the corresponding poly-α-hydroxy acid by using an α-hydroxy acid ammonium salt as a raw material, which process leaves only a small amount of ammonia and can reduce impurities such as by-product α-hydroxy acid amide as much as possible.

Means for Solving the Problems

The present inventors have carried out an extensive investigation. As a result, it has been found that an α-hydroxy acid amide residue in an α-hydroxy acid has an adverse effect such as coloring on the corresponding poly-α-hydroxy acid produced using the α-hydroxy acid as a raw material. It has also been found that the α-hydroxy acid amide is hydrolyzed during a step of bringing a basic metal into contact with an aqueous solution of an α-hydroxy acid ammonium salt to obtain the corresponding α-hydroxy acid metal salt and it is, on the other hand, produced as a by-product by the reverse reaction of the hydrolysis under some conditions.

Moreover, it has been confirmed that when an α-hydroxy acid ammonium salt is obtained by the hydrolysis of an α-hydroxynitrile, impurities such as nitriles, for example, α-aminonitrile or iminodialkylnitrile which is presumed to be a byproduct of the hydrolysis of an α-hydroxynitrile, or amides or carboxylic acids which are hydrolysates of the nitriles remain even if the hydrolysis is performed using a basic metal and such impurities have a serious influence on the quality of an α-hydroxy acid as a polymer raw material.

In addition, it has been found that sufficient progress of the hydrolysis reaction by using the basic metal enables production of an α-hydroxy acid having an adequately reduced content of the above-described impurities and therefore having a sufficient quality as a polymer material; it is optimal to determine the degree of the progress of the hydrolysis reaction of impurities brought by the addition of a basic metal, with a remaining amount of an α-hydroxy acid amide as an index; in particular, in a step of obtaining an α-hydroxy acid metal salt by bringing a basic metal into contact with an aqueous solution of an α-hydroxy acid ammonium salt, an α-hydroxy acid having a sufficiently high quality as a polymer raw material is obtainable by controlling the α-hydroxy acid amide residue in the solution to not greater than 500 [weight ppm/α-hydroxy acid]; and when the α-hydroxy acid thus obtained is used as a raw material, a high quality cyclic dimer ester can be synthesized without causing coloration in the steps of synthesizing an α-hydroxy acid oligomer and depolymerizing the α-hydroxy acid oligomer into the cyclic dimer ester, leading to the completion of the present invention.

The present invention therefore relates to:

[1] a process for producing an α-hydroxy acid, which comprises (1) a step of bringing a basic metal into contact with an aqueous solution of an α-hydroxy acid ammonium salt to produce an α-hydroxy acid metal salt while controlling the concentration of an α-hydroxy acid amide residue in the solution to 500 [weight ppm/α-hydroxy acid] or less and (2) a step of desalting the α-hydroxy acid metal salt into the corresponding α-hydroxy acid;

[2] the process for producing an α-hydroxy acid as described above in [1], wherein in Step (1), the concentration of an ammonia residue in the solution is controlled to 3 [wt. %/α-hydroxy acid] or less;

[3] the process for producing an α-hydroxy acid as described above in [1] or [2], wherein in Step (1), ammonia generated in the step is collected in a gas phase portion;

[4] the process for producing an α-hydroxy acid as described above in [3], wherein the temperature when the ammonia is collected in the gas phase portion is 60° C. or greater;

[5] the process for producing an α-hydroxy acid as described above in any one of [1] to [4], wherein the aqueous solution of an α-hydroxy acid ammonium salt is obtained by the hydrolysis reaction of an α-hydroxynitrile;

[6] the process for producing an α-hydroxy acid as described above in [5], wherein the hydrolysis reaction of an α-hydroxynitrile is an enzymatic catalytic reaction using nitrilase and/or combination of nitrile hydratase and amidase;

[7] the process for producing an α-hydroxy acid as described above in [5], wherein the hydrolysis reaction of an α-hydroxynitrile is performed using nitrilase;

[8] the process for producing an α-hydroxy acid as described above in [6] or [7], wherein the nitrilase is derived from genus *Acinetobacter*;

[9] the process for producing an α-hydroxy acid as described above in [8], wherein the nitrilase is derived from *Acinetobacter* sp. AK226;

[10] the process for producing an α-hydroxy acid as described above in any of [1] to [9], wherein the basic metal is at least one selected from the group consisting of hydroxides, oxides, and carbonates of an alkali metal, beryllium, or magnesium and in Step (2), the α-hydroxy acid metal salt is desalted by ion exchange;

[11] the process for producing an α-hydroxy acid as described above in any one of [1] to [9], wherein the basic metal is at least one selected from the group consisting of hydroxides, oxides, and carbonates of an alkali metal, beryllium, or magnesium and in Step (2), the α-hydroxy acid metal salt is desalted by electrodialysis;

[12] the process for producing an α-hydroxy acid as described above in any one of [1] to [9], wherein the basic metal is at least one selected from the group consisting of hydroxides, oxides, and carbonates of calcium, strontium, barium, or radium and in Step (2), the α-hydroxy acid metal salt is desalted by the addition of sulfuric acid;

[13] the process for producing an α-hydroxy acid as described above in [12], wherein after Step (1), the α-hydroxy acid in solid form is collected by solid-liquid separation and then, washed and in Step (2), sulfuric acid is added to the α-hydroxy acid metal salt in solid form or a slurry obtained by adding water thereto;

[14] the process for producing an α-hydroxy acid as described above in [12] or [13], wherein the basic metal is at least one selected from the group consisting of calcium hydroxide, calcium oxide, and calcium carbonate;

[15] the process for producing an α-hydroxy acid as described above in any one of [1] to [14], which further comprises, after Step (2), a step of removing an impurity anion by using an anion exchange resin and a step of removing an impurity cation by using a cation exchange resin;

[16] the process for producing an α-hydroxy acid as described above in [15], wherein the impurity cation contains either one of a byproduct α-amino acid or iminodialkyl acid;

[17] the process for producing an α-hydroxy acid as described above in any one of [1] to [16], wherein the α-hydroxy acid is lactic acid or glycolic acid;

[18] the process for producing an α-hydroxy acid as described above in [17], wherein the α-hydroxy acid is glycolic acid;

[19] a process for producing a cyclic dimer ester comprising a step of synthesizing an α-hydroxy acid oligomer using, as a raw material, an aqueous solution of an α-hydroxy acid obtained by the process as described above in any one of [1] to [18] and a step of depolymerizing the α-hydroxy acid oligomer; and

[20] a process for producing a poly-α-hydroxy acid comprising a step of conducting a ring-opening polymerization reaction using, as a raw material, the cyclic dimer ester obtained by the process as described above in [19].

Effect of the Invention

According to the production process of an α-hydroxy acid relating to the present invention, an α-hydroxy acid having a sufficiently reduced impurity content and having a sufficiently high quality as a raw material for a poly-α-hydroxy acid can be obtained by controlling, in a production step of an α-hydroxy acid metal salt by bringing a basic metal into contact with an aqueous solution of an α-hydroxy acid ammonium salt, an α-hydroxy acid amide amount remaining in the aqueous solution to not greater than 500 [weight ppm/ α-hydroxy acid]. When the α-hydroxy acid obtained in the process of the present invention is employed as a raw material, a high quality cyclic dimer ester can be synthesized without causing coloration in each of steps for synthesizing an α-hydroxy acid oligomer and for synthesizing a cyclic dimer ester by the depolymerization of the α-hydroxy acid oligomer.

BEST MODE FOR CARRYING OUT THE INVENTION

Although the α-hydroxy acid ammonium salt to be used for the production process of an α-hydroxy acid according to the present invention may be produced by any process, for example, those prepared by the enzymatic catalytic hydrolysis of an α-hydroxynitrile synthesized from hydrocyanic acid and an aldehyde or a ketone are useful.

Although any enzyme catalyst is usable for the hydrolysis of an α-hydroxynitrile insofar as it has a hydrolytic capacity of the nitrile, single use of nitrilase, combined use of nitrile hydratase and amidase, or combined use of nitrilase, nitrile hydratase, and amidase is preferred.

As the nitrilase, nitrile hydratase, or amidase enzyme, those derived from microorganisms, animal/plant cells or the like can be used, but those derived from a microorganism cell is preferred from the viewpoint of an enzyme expression level per weight or handling ease. Many microorganism species are known. Examples of those having a high nitrilase activity include the genus *Rhodococcus*, the genus *Acinetobacter*, the genus *Alcaligenes*, the genus *Pseudomonas*, and the genus *Corynebacterium*. Examples of those having a high nitrile hydratase activity and a high amidase activity include the genus *Rhodococcus* and the genus *Pseudomonas*. For the production of the α-hydroxy acid ammonium salt relating to the present invention, those having high nitrilase activity are especially preferred, of which the genus *Acinetobacter* and the genus *Alcaligenes* which are gram negative bacteria are especially preferred, with the genus *Acinetobacter* being still more preferred. Specific examples include *Acinetobacter* sp. AK226 (FERM BP-08590) and *Acinetobacter* sp. AK227 (FERM BP-08591).

"Remarks to Deposited Biological Material 1"
1) Name and address of the depository:
 The International Patent Organism Depositary, National Institute of Advanced Industrial Science and Technology, Independent Administrative Institution Central 6, 1-1-1 Higashi, Tsukuba-shi, Ibaraki, Japan (Postal code: 305-8566)
2) Date of deposit: Jan. 7, 2004 (date of original deposit)
3) Accession Number: FERM BP-08590

The enzyme catalyst may be a microorganism having a natural nitrilase gene or artificially modified nitrilase gene incorporated therein by genetic engineering or a nitrilase enzyme extracted from the resulting microorganism. It takes more reaction time for producing an α-hydroxy acid ammonium salt by using a small amount of a microorganism with a low expression level of nitrilase or a small amount of a microorganism which expresses nitrilase having a low conversion activity from a nitrile compound to an ammonium carboxylate. It is therefore desired to use a microorganism expressing nitrilase at a level as high as possible, a microorganism expressing nitrilase having a high conversion activity, or a nitrilase enzyme extracted therefrom.

With regard to the form of the enzyme catalyst, a microorganism or animal/plant cell may be used as is; a microorganism or animal/plant cell may be used after treatment such as homogenization; or a necessary nitrilase enzyme extracted from the microorganism or animal/plant cell may be used. These enzyme catalysts may be used as are or may be immobilized using a commonly employed method such as entrapment method, crosslinking method, or support binding method. Examples of the support to be used for immobilization include, but not limited to, glass beads, silica gel, polyurethane, polyacrylamide, polyvinyl alcohol, carrageenan, alginic acid, and photocrosslinkable resin.

When the microorganism or animal/plant cell is used as is, it may be suspended in water (distilled water and/or ion exchange water) alone, but it is the common practice to suspend it in a buffer solution in consideration of an osmotic pressure. As the buffer to be used for this purpose, ordinarily employed inorganic salts such as phosphate buffer are usable, but buffers using an α-hydroxy acid ammonium salt, which is a reaction product, are most preferred in order to minimize contamination of impurities. When the enzyme catalyst is used in an immobilized form, it is ordinarily suspended in a buffer solution in consideration of an osmotic pressure. The concentration of the buffer solution is preferably as low as possible from the viewpoint of reducing an impurity content in the reaction mixture, but is typically less than 0.1M, preferably from 0.01 to 0.08M, more preferably from 0.02 to 0.06M from the viewpoint of stability of the enzyme and maintenance of the enzymatic activity.

The hydrolysis reaction of the α-hydroxynitrile is effected preferably at a pH of from 6 to 8, more preferably at a pH of from 6.5 to 7. Since an α-hydroxynitrile is a very instable substance, an acid component such as sulfuric acid, phosphoric acid, or an organic acid is ordinarily added as a stabilizer. It is therefore essential to add an alkali to the reaction system in order to adjust the pH in the reaction system. Although the alkali to be used for this purpose is not particularly limited insofar as it does not have an influence on the reaction, use of ammonia which is one of the products is preferred. Ammonia may be provided either as an ammonia gas or aqueous ammonia, but aqueous ammonia is ordinarily preferred from the viewpoint of handling ease. The reaction temperature is preferably from 30 to 60° C., more preferably from 40 to 50° C. When the reaction temperature is too low, the reaction activity decreases and it takes more reaction time for the production of a high-concentration α-hydroxy acid ammonium salt. When the reaction temperature is too high, on the other hand, the enzyme is deteriorated due to the heat, and, when the intended concentration of the α-hydroxy acid ammonium salt is high, it becomes difficult to increase the concentration to the intended concentration. As a result, treatment such as further addition of the enzyme becomes necessary, which raises a cost for the catalyst. In addition, a too high reaction temperature leads to acceleration of decomposition of the substrate α-hydroxynitrile into hydrocyanic acid and an aldehyde or a ketone, which may cause further deterioration of reaction activity such as reaction inhibition or deactivation.

The hydrolysis reaction of the α-hydroxynitrile may be carried out in any of a fixed bed, a moving layer, a fluidized layer, and a stirring tank. It may be either a continuous reaction or a semi-batch reaction. When a non-immobilized microorganism strain is used, a semi-batch reaction using a stirring tank is preferred from the viewpoint of ease of the reaction. In this case, appropriate stirring is preferred from the viewpoint of a reaction efficiency. In the semi-batch reaction, the enzyme catalyst of each batch may be disposable or the enzyme catalyst may be used for the reaction in repetition. In the latter case, care should be taken because the specific activity of the enzyme catalyst may deteriorate due to an influence of the osmotic pressure caused by a drastic change in the concentration of the α-hydroxy acid ammonium salt from high to low.

The steady concentration of the α-hydroxynitrile, the reaction substrate, is controlled to preferably 2 wt. % or less, more preferably from 0.1 to 1.5 wt. %, still more preferably from 0.1 to 1.0 wt. %, most preferably from 0.2 to 0.5 wt. %. Too high concentrations of the α-hydroxynitrile may terminate the reaction which has so far proceeded, because a side reaction with ammonia liberated from the ammonium salt of glycolic acid, which is a product, becomes marked and the influence of substrate inhibition or enzyme deactivation which will be marked for the first time at a high product accumulation concentration increases drastically. Too low concentrations of the α-hydroxynitrile are, on the other hand, disadvantageous because they reduce the reaction speed and the α-hydroxy acid ammonium salt cannot be produced efficiently. It is therefore very important to control the steady concentration of the α-hydroxynitrile during the reaction.

A weight ratio of the dry enzyme catalyst to the α-hydroxy acid ammonium salt to be produced is preferably not greater than 1/100, more preferably from 1/100 to 1/500, still more preferably from 1/200 to 1/500, still more preferably from 1/300 to 1/500. Too high weight ratios of the dry enzyme catalyst to the α-hydroxy acid ammonium salt to be produced are not preferred because impurities derived from the suspension of the enzyme catalyst appear in the reaction solution, raise a purification cost, and deteriorate the product quality. On the other hand, too low weight ratios of the dry enzyme catalyst to the α-hydroxy acid ammonium salt to be produced are economically disadvantageous, because they decrease the productivity per reactor volume and a reactor with a large size becomes necessary.

From the hydrolysate of the α-hydroxynitrile thus obtained, the cell or processed product thereof is removed by filtration, centrifugal separation, MF treatment, or the like and an aqueous solution of the α-hydroxy acid ammonium salt is obtained. Treatment with activated carbon may be performed further in order to remove a coloring material and/or a material causing coloration. Examples of the activated carbon usable here include, but not limited to, ordinarily employed coconut shell activated carbon and synthetic activated carbon. The amount of the activated carbon is not limited insofar as it can reduce the coloring material and/or the material causing coloration to a target amount.

Specific examples of the α-hydroxy acid ammonium salt include ammonium salts of glycolic acid, lactic acid, mandelic acid, α-hydroxybutyric acid, α-hydroxyisobutyric acid, α-hydroxy-4-methylthiobutyric acid, α-hydroxy-2-methylpropionic acid, α-hydroxy-2-phenylpropionic acid, α,β-dihydroxy-3,3-dimethylbutyric acid, α-hydroxy-3-butenoic acid, α-hydroxy-3-methyl-3-butenoic acid, or 2-pyridinyl-α-hydroxyacetic acid.

Step (1) of adding a basic metal salt to the aqueous solution of an α-hydroxy acid ammonium salt to prepare the α-hydroxy acid metal salt will hereinafter be described.

Any basic metal is usable in the present invention insofar as it is a basic metal which has a higher basicity than that of ammonia; efficiently provides an α-hydroxy acid metal salt without generating an undesirable by-product when it is brought into contact with the aqueous solution of an α-hydroxy acid ammonium salt; and permits collection of ammonia in a gas phase portion by heat treatment. Specific examples include lithium oxide, lithium hydroxide, lithium carbonate, sodium oxide, sodium hydroxide, sodium carbonate, potassium oxide, potassium hydroxide, potassium carbonate, rubidium oxide, rubidium hydroxide, rubidium carbonate, cesium oxide, cesium hydroxide, cesium carbonate, francium oxide, francium hydroxide, francium carbonate, beryllium oxide, beryllium hydroxide, beryllium carbonate, magnesium oxide, magnesium hydroxide, magnesium carbonate, calcium oxide, calcium hydroxide, calcium carbonate, strontium oxide, strontium hydroxide, strontium carbonate, barium oxide, barium hydroxide, barium carbonate, radium oxide, radium hydroxide, and radium carbonate.

With the aqueous solution of an α-hydroxy acid ammonium salt, the basic metal can be mixed as a solid, as an aqueous solution, or as a slurry mixed with water. From the viewpoint of handling ease, when the basic metal has a sufficiently high water solubility at room temperature, it is used preferably as an aqueous solution and when the solubility is low, it is used preferably as a slurry. When the basic metal is used as a slurry, the solid content weight concentration is adjusted to preferably from 10 to 50 wt. %, more preferably from 20 to 40 wt. %, still more preferably from 25 to 35 wt. % in consideration of its fluidity or handling of it under a uniform state while stirring.

An amount of the basic metal is selected arbitrarily from a range of from 0.8 to 1.5 equivalents to the α-hydroxy acid ammonium salt, preferably within a range of from 1.0 to 1.2 equivalents. In the present invention, removal of ammonia generated during the reaction as much as possible is desired in consideration of the quality of the product. It is however necessary to think how to remove ammonia because water solubility of ammonia is high. In this case, the solubility of ammonia decreases when the pH of the reaction mixture is adjusted to fall in an alkaline range so that the basic metal is used in an amount greater than the equivalent of the α-hydroxy acid ammonium salt. Excessive addition of the basic metal however raises an impurity content in the resulting α-hydroxy acid metal salt. From these viewpoints, an adequate amount of the basic metal will be determined automatically.

The concentration of the aqueous solution of an α-hydroxy acid ammonium salt to be used in Step (1) is not particularly limited. As will be described later, however, when desalting is performed by ion exchange or electrodialysis in Step (2), the α-hydroxy acid metal salt obtainable in Step (1) must be dissolved completely without causing precipitation. It is therefore preferred to adjust the concentration of the aqueous solution of an α-hydroxy acid ammonium salt in advance to low enough not to cause precipitation of the α-hydroxy acid metal salt.

In order to reduce the solubility of ammonia, it is also effective to raise the temperature of the reaction mixture. When the temperature of the reaction mixture is raised in the open system, evaporation of water gradually occurs and ammonia is apt to be removed together with water thus evaporated.

The term "temperature when the ammonia is collected in the gas phase portion" as used herein means the temperature when the basic metal is added to the α-hydroxy acid ammonium salt or the temperature of the reaction mixture after addition. The temperature therefore falls within a range exceeding 60° C. to about 100° C., preferably from about 70 to about 100° C., more preferably from about 80 to about 100° C. Within the above-described temperature range, ammonia, together with water, can be collected in the gas phase portion. The temperature is preferably about 100° C. from the standpoint of reducing time spent for removal of ammonia and reduction of an α-hydroxy acid amide.

Step (1) may be performed in an atmospheric pressure or under reduced pressure. When it is performed under reduced pressure, it is desirably performed at a boiling point of water under a preset reduced pressure. In Step (1), introduction of an inert gas such as nitrogen or helium gas into the reaction mixture facilitates removal of ammonia in the gas phase portion. In such a manner, an aqueous solution or slurry of the α-hydroxy acid metal salt from which ammonia has been removed to such a level as not to cause a problem in quality can be obtained.

In Step (1), an α-hydroxy acid amide produced as a byproduct of thermal decomposition of the α-hydroxy acid ammonium salt (the reverse reaction of hydrolysis of the α-hydroxy acid amide and these reactions are equilibrium reactions) or an α-hydroxy acid amide contained as an impurity in the previous step (hydrolysis reaction of the α-hydroxynitrile) can be hydrolyzed into the corresponding α-hydroxy acid metal salt and free ammonia via the α-hydroxy acid ammonium salt. In Step (1), when the α-hydroxy acid amide cannot be removed sufficiently, the α-hydroxy acid amide remains until a later oligomerization step. By the thermal decomposition in the oligomerization step, ammonia is produced again by the reverse reaction and becomes a cause of coloration, which leads to a serious problem.

In Step (1), when the α-hydroxy acid ammonium salt to be used as a raw material is obtained by the hydrolysis reaction of an α-hydroxynitrile, nitriles contained therein as a byproduct of the hydrolysis such as α-aminonitrile and imino dialkyl nitrile, or amides or carboxylic acids which are hydrolysates thereof can be converted into the corresponding carboxylic acid by the hydrolysis with a basic metal. These nitriles, amides, or carboxylic acids also deteriorate the quality of the α-hydroxy acid to be used as a polymer raw material.

In Step (1), however, impurities such as nitriles and carboxylic acids as well as amides including an α-hydroxy acid amide can be decomposed sufficiently by carrying out the hydrolysis reaction until the concentration of the α-hydroxy acid amide residue in the reaction mixture becomes 500 [weight ppm/α-hydroxy acid] or less. The concentration of the α-hydroxy acid amide residue in the reaction mixture is reduced to preferably 200 [weight ppm/α-hydroxy acid] or less, more preferably 100 [weight ppm/α-hydroxy acid] or less, most preferably 1 [weight ppm/α-hydroxy acid] or less.

Those skilled in the art can measure the concentration [weight ppm/α-hydroxy acid] of the α-hydroxy acid amide in the reaction mixture in a known manner. For example, it can be determined by measuring the concentration of the α-hydroxy acid amide and the concentration of the α-hydroxy acid by liquid chromatography and then dividing the former by the latter.

In the present invention, it is also preferred to measure the concentration of an ammonia residue in the reaction mixture as an index of the progress of the hydrolysis reaction with the basic metal. In order to obtain an α-hydroxy acid having a sufficiently high quality, the concentration of an ammonia residue in the reaction mixture in Step (1) is adjusted to 3 [wt. %/α-hydroxy acid] or less, more preferably 1 [wt. %/α-hydroxy acid] or less, still more preferably 0.1 [wt. %/α-hydroxy acid] or less. Step (2) for desalting the α-hydroxy acid ammonium salt obtained in Step (1) to obtain an α-hydroxy acid will next be described. Although the desalting method of the α-hydroxy acid metal salt in Step (2) is not particularly limited and any method is usable, it is preferably selected from (i) ion exchange, (ii) electrodialysis, and (iii) solid-liquid separation, depending on the state of the α-hydroxy acid metal salt thus obtained.

As the desalting method, (i) ion exchange or (ii) electrodialysis is selected when the basic metal used is at least one basic metal selected from the group consisting of hydroxides, oxides, and carbonates of at least one metal selected from beryllium, magnesium and alkali metals. In this case, specific examples of the basic metal include lithium oxide, lithium hydroxide, lithium carbonate, sodium oxide, sodium hydroxide, sodium carbonate, potassium oxide, potassium hydroxide, potassium carbonate, rubidium oxide, rubidium hydroxide, rubidium carbonate, cesium oxide, cesium hydroxide, cesium carbonate, francium oxide, francium hydroxide, francium carbonate, beryllium oxide, beryllium hydroxide, beryllium carbonate, magnesium oxide, magnesium hydroxide, and magnesium carbonate. Of these, sodium hydroxide and potassium hydroxide are preferred.

When (i) ion exchange or (ii) electrodialysis is employed for the desalting, the α-hydroxy acid metal salt must be in the form of an aqueous solution. When a solid is precipitated in Step (1), it is necessary to dilute it with water until the solid is completely dissolved.

There are roughly two methods for desalting the aqueous solution of the α-hydroxy acid metal salt by using ion exchange: one is to use a cation exchange resin and the other one is to use an anion exchange resin. When the cation exchange resin is used, the resin to be employed may be either a strongly acidic cation exchange resin or a weakly acidic cation exchange resin, but a strongly acidic cation exchange resin is preferred. Specific examples include, but not necessarily limited to, DIAION SK1B, DIAION SK104, DIAION SK110, DIAION SK112, DIAION SK116, DIAION PK208, DIAION PK212, DIAION PK216, DIAION PK220, DIAION PK228, DIAION UBK530, DIAION UBK550, DIAION UBK535, and DIAION UBK555 (each, product of Mitsubishi Chemical), Lewatit S100, Lewatit S109, Lewatit SP112, Lewatit STV40, and Lewatit MSD1368 (each, product of Bayer), Amberlite IR120B, Amberlite 120BN, Amberlite IR124, Amberlite 1006F, Amberlite 200CT, and Amberlite 252 (each, product of Organo Corporation), and DOWEX MONOSPHERE 650C, DOWEX MARATHON C, DOWEX HCR-S, and DOWEX MARATHON MSC (each, product of Dow Chemical Company). These cation exchange resins are used after regeneration in a proton (H$^+$) form in advance by a conventional method.

The cation exchange resin is used in a conventional manner in the present invention. Described specifically, either a batch method in which a predetermined amount of a cation exchange resin is added to the aqueous solution of the α-hydroxy acid metal salt or a column method in which the aqueous solution of the α-hydroxy acid metal salt is fed to a cation exchange resin packed in a resin tower. In the batch method, an aqueous solution of an α-hydroxy acid can be obtained by carrying out stirring for a time sufficient for the metal cation to reach the equilibrium adsorption to the cation exchange resin and then collecting the supernatant. In the column method, a liquid which has passed through the resin until leakage of the metal cation from the lower part of the column occurs becomes an aqueous solution of an α-hydroxy acid.

The cation exchange resin must be used so that a total exchange volume of the resin corresponds to the equivalent of the metal cation or greater. It is usually preferred to use the resin in an amount of at least 1.2 times the equivalent of the metal cation in order to remove it more completely. In the column method, it is the common practice to use an excessive amount of the resin in order to extend the time to the breakthrough of the resin or regeneration of the resin.

The temperature at the time of treatment with the resin may be normal temperature, but heating may be conducted if necessary in a range where heat resistance of the resin is guaranteed. The treatment is ordinarily conducted at a temperature 70° C. or less. In the column method, a feed rate of the aqueous solution is preferably within a range of from 1 to 20 in terms of a space velocity (L/L-resin/Hr), preferably from 2 to 10.

In the column method, the resin can be used in repetition if ordinarily washing and regeneration operations (for example, regeneration using a mineral acid such as dilute hydrochloric acid or dilute sulfuric acid) are performed after its breakthrough point at which a mixed amount of the metal cation in the liquid which has passed through the resin is recognized to exceed a specified amount.

When desalting is effected by using an anion exchange resin, the resin may be any of a strongly basic anion exchange resin, a moderately basic anion exchange resin, and a weakly basic anion exchange resin. Of these, a weakly basic or moderately basic anion exchange resin is preferred. Specific examples include Amberlite IRA-93 (product of Organo Corporation), DIAION WA20 and DIAION WA 30 (each, product of Mitsubishi Chemical), and Lewatit MP64 (product of Bayer).

The anion exchange resin is used in a conventional manner in the present invention. Described specifically, either a batch method in which a predetermined amount of an anion exchange resin is added to the aqueous solution of the α-hydroxy acid metal salt or a column method in which the aqueous solution of the α-hydroxy acid metal salt is fed to an anion exchange resin packed in a resin tower. In the batch method, an aqueous solution of an α-hydroxy acid can be obtained by carrying out stirring for a time sufficient for an α-hydroxy acid anion to reach the equilibrium adsorption to the anion exchange resin, collecting and washing the resin, and then treating it with a mineral acid (such as hydrochloric acid, sulfuric acid, or nitric acid). In the column method, after leakage of the α-hydroxy acid anion occurs from the lower portion of the column, an adequate amount of the aqueous solution of an α-hydroxy acid metal salt is fed and this feeding is continued until the solution at the outlet has an equal composition to that of the solution at the inlet so as to adsorb the maximum amount of the α-hydroxy acid anion to the resin. After sufficient washing, a mineral acid (such as hydrochloric acid, sulfuric acid, or nitric acid) is fed to the resin to desorb the α-hydroxy acid anion therefrom to obtain an aqueous solution of an α-hydroxy acid.

The temperature at the time of treatment with the resin may be normal temperature, but heating may be conducted if necessary within a range where heat resistance of the resin is guaranteed. The treatment is ordinarily conducted at a temperature of 70° C. or less. In the column method, a feed rate of the aqueous solution is preferably within a range of from 1 to 20 in terms of a space velocity (L/L-resin/Hr), preferably from 2 to 10.

In the column method, the resin can be used in repetition if ordinarily washing and regeneration operations (for example, regeneration using a strong aqueous alkali solution such as an aqueous solution of sodium hydroxide or an aqueous solution of potassium hydroxide) are performed after the feeding of the aqueous solution is continued further until the solution at the outlet has an equal composition to that of the solution at the inlet with the point, as a breakthrough point, at which a mixed amount of the mineral acid anion in the liquid which has passed through the resin at the time of desorption operation of the α-hydroxy acid anion with the mineral acid is recognized to exceed a specified amount.

In the next place, there are roughly three methods for desalting of the aqueous solution of the α-hydroxy acid metal salt in accordance with electrodialysis. The first one is a method of using a two-compartment water decomposition electrodialyzer in which bipolar films and cation exchange membranes are arranged alternately and an acid compartment and a base compartment are formed and causing a metal cation in the aqueous solution of the α-hydroxy metal salt to move in the cation exchange membrane. The second one is a method of using a two-compartment water decomposition electrodialyzer in which bipolar films and anion exchange membranes are arranged alternately and an acid compartment and a base compartment are formed and causing an α-hydroxy acid anion in the aqueous solution of the α-hydroxy metal salt to move in the anion exchange membrane. The third one is a method of using a three-compartment water decomposition electrodialyzer in which bipolar membranes, cation exchange membranes, and anion exchange membranes are arranged in order and a raw material compartment, an acid compartment, and a base compartment are formed and causing a metal cation in the aqueous solution of the α-hydroxy acid metal salt to move in the cation exchange membrane and causing an α-hydroxy acid anion to move in the anion exchange membrane. Any method can be employed, but a method of using a two-compartment water decomposition electrodialyzer in which bipolar films and cation exchange membranes are arranged alternately and an acid compartment and a base compartment are formed and causing a metal cation in the aqueous solution of the α-hydroxy metal salt to move in the cation exchange membrane is preferred from the viewpoint of the quality of the resulting aqueous solution of an α-hydroxy acid and electric efficiency.

As the bipolar membrane to be used in the present invention, conventionally known bipolar membranes, that is, bipolar membranes having a structure in which a cation exchange membrane and an anion exchange membrane are bonded to each other are usable. Specific examples of it include NEO-SEPTA BP-1 (product of Astom). The cation exchange membrane is, for example, NEOSEPTA CMB (Product of Astom), while the anion exchange membrane is, for example, NEO-SEPTA AHA (product of Astom).

As one example of the electrodialysis step in the present invention, electrodialysis using a two-compartment dialyzer composed of a bipolar membrane and a cation exchange membrane will next be described. In this method, an aqueous solution of an α-hydroxy acid is collected from the acid compartment, while an aqueous solution of a basic metal is collected from the base compartment.

FIG. 1 is a schematic view illustrating a typical example of a water decomposition electrodialyzer to be used in this method. In the water decomposition electrodialyzer illustrated in FIG. 1, two membranes, that is, a bipolar membrane (B) 3 and a cation exchange membrane (C) 4 are arranged alternately and two compartments, that is, an acid compartment 7 and a base compartment 8 are formed between a positive electrode 1 and a negative electrode 2. A space 5 between the bipolar membrane (B) 3 and the positive electrode 1 and another space 6 between the bipolar membrane (B) 3 and the negative electrode 2 are each filled with an electrode solution. In this electrodialyzer, a compartment between the bipolar membrane (B) 3 on the side of the anion exchange body and the cation exchange membrane (C) 4 is functioned as the base compartment 8, while another compartment between the bipolar membrane (B) 3 on the side of the cation exchange body and the cation exchange membrane (C) 4 is functioned as the acid compartment 7.

In the present invention, in the water decomposition electrodialysis step using the above-described known water decomposition electrodialyzer, it is preferred to employ a method of carrying out electrodialysis while disposing an external tank of a liquid to be supplied to each of the acid compartment 7 and the base compartment 8 and circulating the liquid among these compartments and the external tank.

By supplying the acid compartment 7 with the aqueous solution of the α-hydroxy acid metal salt, which is a raw material, and applying a current, a metal cation passes through the cation exchange membrane (C) 4 and enters in the base compartment 8. The metal cation combines with an OH⁻ ion generated at this time from the bipolar membrane (B) 3 to yield an aqueous solution of a basic metal. In the acid compartment 7, on the other hand, a proton generated from the bipolar membrane combines with an α-hydroxy acid anion to yield a non-dissociative α-hydroxy acid. It remains in the acid compartment 7 and can be collected. The water decomposition electrodialysis is performed at a temperature of typically from 5 to 70° C., preferably from 20 to 50° C. The separated aqueous solution of the basic metal salt can be utilized for alkali treatment of the aqueous solution of an α-hydroxy acid ammonium salt in the previous step after concentration or without concentration.

When the basic metal to be used for the hydrolysis of the α-hydroxy acid ammonium salt is at least one basic metal selected from the group consisting of hydroxides, oxides, and carbonates of at least one metal selected from the group consisting of calcium, strontium, barium, and radium, solid-liquid separation is employed as a desalting method. Examples of the basic metal to be used in this case include calcium oxide, calcium hydroxide, calcium carbonate, strontium oxide, strontium hydroxide, strontium carbonate, barium oxide, barium hydroxide, barium carbonate, radium oxide, radium hydroxide, and radium carbonate. Of these, calcium hydroxide and calcium oxide are preferred.

The α-hydroxy acid metal salt obtainable in this case is in a slurry form. An aqueous solution of an α-hydroxy acid and a metal sulfate salt can be formed by directly adding sulfuric acid to the resulting slurry of the α-hydroxy acid metal salt. Alternatively, after solid-liquid separation of the α-hydroxy acid metal salt by centrifugal separation or the like, crystals of the α-hydroxy acid metal salt are washed with water or a saturated aqueous solution of the α-hydroxy acid metal salt to remove impurities and then sulfuric acid can be added to the residue. Washing enables reduction of various impurities which will presumably be mixed in the product and improvement in the quality of an α-hydroxy acid thus obtained.

The concentration of sulfuric acid to be used in this step may fall within any range, but a concentration of 50 wt. % or greater is preferred from the viewpoint of not reducing the concentration of the aqueous α-hydroxy acid solution finally obtained. Concentrated sulfuric acid is more desirable than dilute sulfuric acid from the viewpoint of preventing corrosion of a portion which is brought into contact with sulfuric acid. The concentration of commercially available concentrated sulfuric acid, that is, from about 95 to 98 wt. % is preferred.

Sulfuric acid can be added at a desired temperature. The temperature is desirably from about 50 to 80° C., when the temperature at which the slurry of the α-hydroxy acid metal salt is in a good fluidity condition and a reaction between the α-hydroxy acid metal salt and sulfuric acid is effected efficiently is considered as the lower limit, while the temperature at which no bumping phenomenon due to the heat of the reaction occurs is considered as the upper limit. Sulfuric acid is added in an amount selected from a range of from 0.8 to 1.2 equivalents of the α-hydroxy acid metal salt, preferably from 0.9 to 1.1 equivalents. An amount closer to 1 equivalent is more preferred.

The addition of sulfuric acid to the slurry of the α-hydroxy acid metal salt yields a metal sulfate in a solid form and an aqueous solution of an α-hydroxy acid because of low solubility of the metal sulfate in the aqueous solution of an α-hydroxy acid. The metal sulfate obtainable in this step may be in the form of various hydrates, but it may be crystals in any form.

The aqueous solution of an α-hydroxy acid can be obtained by subjecting the resulting mixture of the aqueous solution of an α-hydroxy acid and the metal sulfate to solid-liquid separation such as centrifugal separation. A portion of the α-hydroxy acid is present in the crystals of the metal sulfate as adhesion water, but the α-hydroxy acid can be collected by washing the crystals of the metal sulfate. Water is typically used for the washing of the metal sulfate. Although the temperature of washing water is not particularly limited, washing may ordinarily be performed at normal temperature. When the α-hydroxy acid metal salt is present in the crystals, use of hot water is recommended from the viewpoint of improvement in the quality of the crystals of the metal sulfate thus obtained. Solubility of the metal sulfate in water has almost no temperature dependence while solubility of the α-hydroxy acid metal salt in water has a high temperature dependence so that the α-hydroxy acid metal salt can be selectively washed and removed by crystal washing with hot water. In this case, the temperature of hot water is from 50 to 100° C., preferably from 50 to 80° C.

Examples of the washing method include washing with nozzles in a centrifugal separator and counterflow contact washing of slurry. It is preferred to efficiently wash the crystals with a less amount of washing water in order to prevent a decrease in the concentration of the aqueous solution of an α-hydroxy acid.

According to the production process of an α-hydroxy acid relating to the present invention, the α-hydroxy acid can be obtained as an aqueous solution, but the aqueous solution of the α-hydroxy acid contains various impurities. When cation exchange is employed for desalting, the aqueous solution contains, as impurities, metal cations which have leaked partially from the resin, ammonium cations, and anionic components which have not been adsorbed to the resin at all. When anion exchange is employed for desalting, the aqueous solution contains, as impurities, metal cations which have remained after washing, ammonium cations, and anionic components showing a similar behavior to that of an α-hydroxy acid.

When electrodialysis is employed for desalting, it is difficult to achieve a desalting efficiency of 100%. Some metal cations and ammonium cations are mixed in the aqueous solution of an α-hydroxy acid and anionic components showing a similar behavior to that of the α-hydroxy acid are contained as impurities.

When solid-liquid separation is employed for desalting, the aqueous solution of an α-hydroxy acid contains, as impurities, metal cations and sulfate anions corresponding to the solubility of the metal sulfate, other metal cations derived from the basic metals used in the previous step, ammonium cations which have remained after the $NH_3$ removal step, amino acids which are byproducts of the enzymatic reaction, trace components which are the cell-derived components of the culture medium, or sulfate anions.

When a large amount of metal cations and impurity anionic components is contained in the aqueous solution of an α-hydroxy acid, it is necessary to reduce their concentrations to adequate ones in order to avoid the influence caused by accumulation of these cations and anions when the synthesis reaction of a cyclic dimer ester in the subsequent step is performed by repeating a batch reaction. In addition, the ammonium cations or amino acids may cause coloration and have an adverse effect on the physical properties of polymer products so that it is desired to reduce their concentrations as much as possible.

Cationic impurities in the reaction mixture such as metal cations and ammonium cations can be purified or removed by an ordinary operation of cation exchange. Even neutral amino acids can also be purified or removed by cation exchange similarly because the equilibrium state is toward cationic in a high-concentration aqueous solution of glycolic acid. Anionic impurities such as sulfate anions can also be purified or removed by an ordinary operation of anionic exchange.

The present invention also embraces a process for producing a cyclic dimer ester, which comprises a step of synthesizing an α-hydroxy acid oligomer by using the aqueous solution of an α-hydroxy acid obtained in the above-described production process of an α-hydroxy acid according to the present invention and a step of depolymerizing the α-hydroxy acid oligomer. The present invention also embraces a process for producing a poly-α-hydroxy acid comprising a step of carrying out ring-opening polymerization of the cyclic dimer ester. Use of the α-hydroxy acid obtained in the process of the present invention makes it possible to obtain a high-quality cyclic dimer ester without causing coloration.

The following is a production process of glycolic acid which is used as an example of an α-hydroxy acid. The process includes the steps until the synthesis of a polymer. The α-hydroxy acid is however not limited to glycolic acid.

In the step of synthesizing a glycolic acid oligomer, a raw material glycolic acid is heated to a temperature of typically from 100 to 250° C., preferably from 140 to 230° C. in the presence of a dehydration condensation catalyst if necessary under reduced pressure or under pressure and a condensation reaction is performed until distillation of water substantially stops. After completion of the condensation reaction, the glycolic acid oligomer thus obtained can be used as is as a raw material for the subsequent step. The glycolic acid oligomer can also be used, after taken out from the reaction system, washed with a non-aqueous solvent such as benzene or toluene to remove an unreacted material, low polymer or catalyst. The glycolic acid oligomer may be either cyclic or linear. The polymerization degree is not particularly limited, but it has preferably a melting point (Tm) of typically 140° C. or greater, preferably 160° C. or greater, more preferably 180° C. or greater from the viewpoint of a production yield of glycolide in the depolymerization reaction. The term "Tm" means a melting point of the glycolic acid oligomer detected by heating at a rate of 10° C./min in an inert gas atmosphere by using a differential scanning calorimeter.

The depolymerization method in the step of depolymerizing the glycolic acid oligomer to yield a glycolide is not particularly limited and ordinarily employed melting depolymerization or solid-phase depolymerization can be employed. The depolymerization system in this case can be classified roughly into two systems, that is, a system substantially composed only of the glycolic acid oligomer and a system containing the glycolic acid oligomer and a polar organic solvent.

When the depolymerization reaction system substantially composed only of the glycolic acid oligomer is heated under normal pressure or under reduced pressure, glycolide generated by the depolymerization reaction sublimes or evaporates. By a method of blowing an inert gas into the depolymerization reaction system or the like method to discharge the glycolide out of the system, the glycolide can be obtained.

When the depolymerization reaction system composed of a mixture containing the glycolic acid oligomer and a polar organic solvent is heated, on the other hand, codistillation of the glycolide produced by the depolymerization reaction and the polar organic solvent occurs. From the distillate, the glycolide is separated by crystallization or the like method and then, the glycolide thus separated can be collected. Also in this case, a depolymerization reaction is performed by heating the depolymerization reaction system under normal pressure or under reduced pressure.

As the depolymerization method, a solution depolymerization method in which the glycolic acid oligomer is depolymerized in a solution phase is preferred from the viewpoint of prevention of the glycolic acid oligomer to be used as a raw material from becoming a heavy duty material or production efficiency of glycolide.

The glycolide obtained in the present invention can be converted into polyglycolic acid by the ring-opening polymerization. The ring-opening polymerization is performed typically at a temperature of 100° C. or greater, preferably from about 160 to 180° C. in the presence of a catalyst. The catalyst is not particularly limited and any catalyst is usable insofar as it is used as a ring-opening polymerization catalyst of various cyclic esters. Specific examples include oxides, halides, carboxylates, and alkoxides of a metal compound containing, for example, tin (Sn), titanium (Ti), aluminum (Al), antimony (Sb), zirconium (Zr), or zinc (Zn). The catalyst is used usually in a small amount relative to the cyclic ester. It is used typically in an amount of from 0.0001 to 0.5 wt. %, preferably from 0.001 to 0.1 wt. % based on the cyclic ester.

EXAMPLES

In the following examples, the details of the present invention will be described more specifically by using glycolic acid and lactic acid as examples of the α-hydroxy acid but the present invention is not necessarily limited to these acids.

<Measurement Method of Weight of Dried Cell Catalyst>

The weight of a dried cell catalyst in a cell suspension was measured in the following manner. After an appropriate amount of the cell catalyst suspension having an adequate concentration was weighed and cooled to −80° C., it was dried completely by using a freeze dryer. From the weight value, the concentration of the cell catalyst suspension was calculated. The cell catalyst suspension having a known concentration was diluted to plural appropriate concentrations and transmittance (600 nm) at room temperature was measured using a spectrophotometer. A calibration curve of the cell catalyst obtained using the spectrophotometer was plotted. From the reading of the spectrophotometer, the concentration of the dried cell catalyst in the cell catalyst suspension was then calculated.

<Analysis Method of Reaction Mixture>

The reaction mixture and the reaction mixture after treatment were analyzed in the following manner. Glycolonitrile which was a substrate, glycolic acid (ammonium) and lactic acid (ammonium) which were products, and glycoloamide and lactic acid amide which were byproducts were analyzed by high-performance liquid chromatography under the following conditions: use of ion exclusion column (Shim-pack SCR-101H, product of Shimadzu) as a column, column temperature at 40° C., use of an aqueous phosphoric acid solution (pH=2.3) as a mobile phase, a flow rate of 0.7 cc/min, and use of UV (SPD-10Avvp, product of Shimadzu, 210 nm) and RI (RID-6A, product of Shimadzu) as a detector.

Glycine, iminodiacetic acid, alanine, and iminodiisopropionic acid, which were other byproducts, were analyzed using an ion pair chromatographic system (Hitachi D-7000) using an ion pairing agent under the following conditions: use of ODS-80TS (product of TOSOH) as a column, a column temperature at 40° C., use of a 50 mM aqueous phosphoric acid solution+a 10 mM sodium pentasulfonate solution, a flow rate of 0.5 cc/min, use of RI (RID-6A, product of Shimadzu), and an injection amount of 10 μL.

The sodium ion, calcium ion, and ammonium ion in the reaction mixture and the reaction mixture after treatment were analyzed by ion chromatography under the following conditions: use of a cation exchange column (Tsk gel IC-Cation, product of TOSOH) as a column, a column temperature at 40° C., use of a 2 mM aqueous nitric acid solution as a mobile phase, a flow rate of 0.5 cc/min, and use of a conductivity detector ("CM-8020", product of TOSOH) as a detector.

The sulfate ion in the reaction mixture and the reaction mixture after treatment was analyzed by ion chromatography under the following conditions: use of an anion exchange column (Tsk gel IC-Anion SW, product of TOSOH) as a column, a column temperature at 40° C., use of an eluent for anion analysis (product of TOSOH) as a mobile phase, a flow rate of 1.2 cc/min, and use of a conductivity detector (CM-8020, product of TOSOH) as a detector.

Synthetic glycolide and lactide were analyzed by gas chromatography under the following conditions: use of FID as a detector, use of a medium polarity capillary column (DB-1701, product of J&W SCIENTIFIC, length: 60 m, inner diameter: 0.25 mm, film thickness: 1 μm), use of helium (300 kPa) as a carrier, injection temperature at 200° C., detector temperature at 200° C., and operation temperature at 100° C.×5 minutes, 20° C./min., and 270° C.×10 minutes.

<Preparation of Enzyme Catalyst>

An Erlenmeyer flask was charged with 250 ml of a culture medium containing 0.1 wt. % of sodium chloride, 0.1 wt. % of potassium dihydrogen phosphate, 0.05 wt. % of magnesium sulfate heptahydrate, 0.005 wt. % of ferrous sulfate heptahydrate, 0.1 wt. % of ammonium sulfate, 0.1 wt. % of potassium nitrate, and 0.005 wt. % of manganese sulfate pentahydrate. The culture medium was adjusted to pH 7 with sodium hydroxide. After sterilization at 121° C. for 20 minutes, 0.5 wt. % of acetonitrile was added. The resulting mixture was inoculated with *Acinetobacter* sp. AK226, followed by shaking culture (preculture) at 30° C. A 5-L jar fermenter was charged with 3 L of a culture medium containing 0.3 wt. % of meast powder, 0.5 wt. % of sodium glutaminate, 0.5 wt. % of ammonium sulfate, 0.2 wt. % of dipotassium hydrogen phosphate, 0.15 wt. % of potassium dihydrogen phosphate, 0.1 wt. % of sodium chloride, 0.18 wt. % of magnesium sulfate heptahydrate, 0.02 wt. % of manganese chloride tetrahydrate, 0.01 wt. % of calcium chloride dihydrate, 0.003 wt. % of iron sulfate heptahydrate, 0.002 wt. % of zinc sulfate heptahydrate, 0.002 wt. % of copper sulfate pentahydrate, and 2 wt. % of soybean oil. After sterilization at 121° C. for 20 minutes, the resulting sterilized culture medium was inoculated with the above-described preculture medium, followed by aerated stirring. Ten hours after cultivation was started, feeding of soybean oil was started. The mixture was adjusted to pH 7 with phosphoric acid and aqueous ammonia and an about 5 wt. % *Acinetobacter* sp. AK226 suspension was obtained finally. The resulting suspension was washed twice with a 0.06M phosphate buffer to obtain an *Acinetobacter* sp. AK226 suspension (dried cell concentration of 5 wt. %) in the phosphate buffer.

<Preparation of Aqueous Ammonium Glycolate Solution>

A 1-L four-necked flask was charged with 1.8 g of the *Acinetobacter* sp. AK226 suspension (5.1 wt. %) obtained as described above and 225 g of distilled water to suspend the former in the latter. The flask was equipped with a pH meter and a thermometer to monitor the pH and the temperature of the reaction mixture and placed in a temperature-controlled water bath of 50° C. Stirring was performed with a stirrer and the reaction mixture was maintained for a while until the internal temperature became 50° C. The water bath was then fed with a 55 wt. % aqueous glycolonitrile solution (product of Tokyo Chemical Industry) as a raw material by using a liquid chromatography pump at a feed rate of 0.33 g/min. In order to neutralize sulfuric acid contained, as a stabilizer, in the raw material glycolonitrile, 1.5 wt. % aqueous ammonia was fed through a tube pump. The aqueous ammonia feed pump was set to control the pH of the internal solution to 6.9±0.1 by the pH meter. During the reaction, sampling was performed periodically and the concentrations of glycolonitrile and ammonium glycolate were measured using high-performance liquid chromatography. The addition amount of the raw material was adjusted to give a steady glycolonitrile concentration of 2 wt. % or less. The final accumulation concentration of ammonium glycolate was 52 wt. % and glycolonitrile as a substrate was not detected. The aqueous solution of ammonium glycolate thus obtained was treated using a centrifugal separator (High-speed centrifuge 7700, product of Kubota Corporation) under the conditions of a rotation speed of 10000 pm, treatment time of 20 minutes, and treatment temperature of 4° C. After the supernatant was collected, treatment was performed using MF (PSP-003, product of Asahi Kasei Chemicals) at a flow rate of 2 ml/min and a treatment temperature of 30° C. to yield 1065 g of a 52 wt. % aqueous solution of ammonium glycolate. Since the resulting solution was colored a little, 0.83 g of commercially available activated carbon (Shirasagi A, product of Nippon Envirochemicals) was added and the resulting mixture was stirred at room temperature for 45 minutes. The treated solution was collected by decantation and the coloring component was removed. The concentrations of ammonium glycolate and a byproduct glycoloamide in the resulting aqueous solution of ammonium glycolate were 52 wt. % and 0.33 wt. %, respectively.

<Preparation of Aqueous Solution of Ammonium Lactate>

The aqueous solution of ammonium lactate used in the following Examples was obtained by adding commercially available 97% lactic acid amide (product of Wako Pure Chemicals) to commercially available 40% ammonium lactate (product of Wako Pure Chemicals). The resulting aqueous solution had an ammonium lactate concentration of 40 wt. % and a lactic acid amide concentration of 0.35 wt. %.

Example 1

A 1-L four-necked flask was charged with 400 g of a 52 wt. % aqueous solution of ammonium glycolate. The flask was equipped with, at the side tube thereof, a thermometer, a reflux apparatus, and a capillary for $N_2$ bubbling and, at the center, a three-one motor stirring blade and the whole system was dipped in a temperature-controlled water bath. The internal temperature was raised to 70° C. while carrying out $N_2$ bubbling. To the reaction mixture was added dropwise 225 g of a 40 wt. % aqueous solution of sodium hydroxide in portions. After operation at normal temperature for 20 minutes, the pressure was reduced gradually by a vacuum pump to a final pressure of 140 mmHg. The N bubbling was continued during pressure reduction and the internal temperature became 63° C.

The deammoniation operation was continued for 2 hours under the above-described conditions to yield a 36.9 wt. % aqueous solution of crude sodium glycolate. Finally, an ammonia concentration was 0.241 [wt. %/glycolic acid] or less, a glycine concentration was 1.78 [wt. %/glycolic acid], an iminodiacetic acid concentration was 0.080 [wt. %/glycolic acid], and a deammoniation efficiency was 98.8% or greater. No glycoloamide was detected.

Without interruption, 70 mL of a commercially available strongly-acidic cation exchange resin (Amberlite IR120B) which had been regenerated in a proton form in advance was suspended in pure water. The resulting suspension was filled in a column made of glass and having a diameter of 1.4 cm. After sufficient washing, the solution (aqueous solution of sodium glycolate) after the deammoniation operation was fed to the column at a flow rate of 4.7 mL/min. Using a fraction collector, the solution was collected in an amount of 10 ml/tube. Fractions just before occurrence of the leakage of sodium cations based on the analysis results were mixed and the mixture was designated as a collected solution. None of ammonium cations, sodium cations, glycine and iminodiacetic acid was detected from the collected solution.

Without interruption, 70 mL of a commercially available weakly-acidic anion exchange resin (Amberlite IRA96SB) which had been regenerated in an OH form in advance was suspended in pure water. The resulting suspension was filled in a column made of glass and having a diameter of 1.4 cm. After sufficient washing, the aqueous solution of glycolic acid subjected to cation exchange treatment was fed at a flow rate of 4.7 mL/min. Using a fraction collector, the solution was collected in an amount of 10 ml/tube. Fractions just before occurrence of the leakage of impurity anionic components (sulfate anions, phosphate anions, or the like derived from the culture medium) based on the analysis results were mixed. The mixture was designated as a collected solution. Neither sulfate anions nor phosphate anions were detected from the collected solution.

A portion of the resulting aqueous solution of glycolic acid was charged in a 50-mL eggplant type flask. After the flask was purged with nitrogen, heating was started under a nitrogen flow. While stirring with a stirrer at normal pressure, the reaction mixture was heated from 170 to 200° C. A condensation reaction was effected while distilling off water thus generated. Low boiling point substances such as unreacted glycolic acid were distilled off by reducing the pressure to 40 mmHg with a vacuum pump and heating the reaction mixture at 200° C. for 2 hours. The prepolymer thus obtained was substantially colorless and transparent.

A depolymerization reaction was then effected by raising the temperature to 260° C. and the pressure reduction degree to from 3 to 5 mmHg. The distillate was collected in a cold trap with ice water. As a result of gas chromatographic analysis, no peak other than that of glycolide was observed. The residue in the flask was lightly colored, but the glycolide in the trap was almost colorless.

Example 2

As in Example 1, ammonium glycolate was subjected to deammoniation operation to yield 583 g of a 37.2 wt. % aqueous solution of crude sodium glycolate having an ammonia concentration of 0.225 [wt. %/glycolic acid] and glycoloamide not greater than a detection limit (1 weight ppm).

Without interruption, cation exchange membranes NEOSEPTA CMB (4 of FIG. 1) (product of Astom) and bipolar membranes NEOSEPTA BP-1 (3 of FIG. 1) (product of Astom) were arranged alternately to form 10 membrane pairs (effective membrane area: 550 $cm^2$) and acid compartments (7 of FIG. 1) and base compartments (8 of FIG. 1), and electrode compartments (5 and 6 of FIG. 1) were formed by using "Acilyzer EX3B" (product of Astom) as an electrodialyzer. The acid compartments were each equipped with a tank for the aqueous solution of crude sodium glycolate; the base compartments were each equipped with a tank for a 0.4 wt. % aqueous sodium hydroxide solution; and the electrode compartments were each equipped with a tank for a 2.0 wt. % aqueous solution of sodium hydroxide, respectively. These solutions were supplied and circulated. A raw material compartment was equipped with a cooling jacket and electrodialysis was performed for 2 hours at a treatment temperature of 40° C. or less and a constant voltage of 30 V (electric current depending on the situation). As a result, 439 g of an aqueous glycolic acid solution having a glycolic acid concentration of 33.1 wt. %, an ammonia concentration of 12 wt·ppm, and a sodium concentration of 480 wt. ppm was obtained from the acid compartment.

Without interruption, 70 mL of a commercially available weakly-basic anion exchange resin (Amberlite IRA96SB) which had been regenerated in an OH form in advance was suspended in pure water. The resulting suspension was filled in a column made of glass and having a diameter of 1.4 cm. After sufficient washing, the aqueous glycolic acid solution subjected to the electrodialysis treatment was fed at a flow rate of 4.7 mL/min. Using a fraction collector, the solution was collected in an amount of 10 ml/tube. Fractions just before occurrence of the leakage of impurity anionic components (sulfate anions, phosphate anions, and the like derived from the culture medium,) based on the analysis results were mixed. The mixture was designated as a collected solution. Neither sulfate anions nor phosphate anions were detected from the collected solution.

Without interruption, 70 mL of a commercially available strongly-acidic cation exchange resin (Amberlite IR120B) which had been regenerated in a proton form in advance was suspended in pure water. The resulting suspension was filled in a column made of glass and having a diameter of 1.4 cm.

After washing sufficiently, the aqueous glycolic acid solution subjected to the anion exchange treatment was fed at a flow rate of 4.7 mL/min. Using a fraction collector, the solution was collected in an amount of 10 ml/tube. Fractions just before occurrence of the leakage of sodium cations based on the analysis results were mixed. The mixture was designated as a collected solution. None of ammonium cations, sodium cations, glycine and iminodiacetic acid was detected from the collected solution.

A portion of the resulting aqueous glycolic acid solution was charged in a 50-mL eggplant type flask. After the flask was purged with nitrogen, heating was started under a nitrogen flow. While stirring with a stirrer at normal pressure, the temperature was raised from 170° C. to 200° C. A condensation reaction was effected while distilling off water thus generated. Low boiling point substances such as unreacted glycolic acid were then distilled off by reducing the pressure to 40 mmHg with a vacuum pump and heating the reaction mixture at 200° C. for 2 hours. The prepolymer thus obtained was substantially colorless and transparent. A depolymerization reaction was effected while raising the temperature to 260° C. and the pressure reduction degree to from 3 to 5 mmHg. The distillate was collected in a cold trap with ice water. As a result of gas chromatographic analysis, no peak other than that of glycolide was observed. The residue in the flask was lightly colored, but the glycolide in the trap was almost colorless.

Comparative Examples 1 and 2, Examples 3 and 4

A 100-mL four-necked flask was charged with 50 g of a 52 wt. % aqueous solution of ammonium glycolate. The flask was equipped with, at the side tube thereof, a thermometer and a reflux apparatus and, at the center, a three-one motor stirring blade and the whole system was dipped in a temperature-controlled water bath. The internal temperature was raised to 40, 60, 80, or 100° C. A 30 wt. % calcium hydroxide slurry (37.9 g) was added dropwise over 15 minutes. This means that 0.55 mol of calcium hydroxide was used per mol of ammonium glycolate.

After treatment for hours as shown in Table 1, the calcium glycolate slurry thus obtained was sampled. After the sample was diluted with distilled water to an adequate concentration, a glycol acid concentration and a glycoloamide concentration were analyzed by high performance liquid chromatography, while an ammonia concentration was analyzed by ion chromatography. An ammonia wt. % and glycolamide concentration per weight of glycolic acid were determined. The results are shown in Table 1 an FIG. 2.

TABLE 1

| | Reaction temperature [° C.] | Reaction time [Hr] | $NH_3$ residue [wt. %/GA] | Amide residue [wt · ppm/GA] |
|---|---|---|---|---|
| Comp. Ex. 1 | 50 | 9 | 5.9 | 2895 |
| Comp. Ex. 2 | 60 | 7 | 6.1 | 997 |
| Example 3 | 80 | 2.5 | 3.0 | 180 |
| Example 4 | 100 | 1.5 | 0.063 | ND |

A portion of the calcium glycolate slurry obtained in Example 3 was filtered through a funnel with a glass filter. To the wet crystals of calcium glycolate thus obtained was added the same weight of distilled water heated to 50° C.; the resulting mixture was stirred using a spatula; and the reaction mixture was filtered through a funnel with a glass filter. This operation was repeated three times. To a portion of the wet crystals of calcium glycolate thus obtained, 50 wt. % sulfuric acid was added to give a molar ratio of 1.03 per mol of calcium glycolate while keeping the temperature at 60° C. The reaction mixture was then saturated for one hour. The crystals of calcium sulfate thus obtained were filtered and separated through a funnel with a glass filter and a 54.1 wt. % aqueous glycolic acid solution was obtained as a filtrate.

The concentration of the other impurities in the aqueous glycolic acid solution was analyzed. As a result, 3400 wt·ppm/GA of calcium cations, 6500 wt·ppm/GA of sulfate anions and 2 wt·ppm/GA or less of ammonia were detected. Glycoloamide was not detected.

Without interruption, 70 mL of a commercially available weakly-acidic anion exchange resin (Amberlite IRA96SB) which had been regenerated in an OH form in advance was suspended in pure water. The resulting suspension was filled in a column made of glass and having a diameter of 1.4 cm. After sufficient washing, the aqueous glycolic acid solution obtained by the solid-liquid separation treatment was fed at a flow rate of 4.7 mL/min. Using a fraction collector, the solution was collected in an amount of 10 ml/tube and fractions just before occurrence of the leakage of impurity anionic components (sulfate anions) based on the analysis results were mixed. The mixture was designated as a collected solution. Sulfate anions were not detected from the collected solution.

Without interruption, 70 mL of a commercially available strongly-acidic cation exchange resin (Amberlite IR120B) which had been regenerated in a proton form in advance was suspended in pure water. The resulting suspension was filled in a column made of glass and having a diameter of 1.4 cm. After sufficient washing, the aqueous glycolic acid solution subjected to the anion exchange treatment was fed at a flow rate of 4.7 mL/min. Using a fraction collector, the solution was collected in an amount of 10 ml/tube. Fractions just before occurrence of the leakage of calcium cations based on the analysis results were mixed and the mixture was designated as a collected solution. None of ammonium cations, calcium cations, glycine and iminodiacetic acid was detected from the collected solution.

A portion of the resulting aqueous solution of glycolic acid was charged in a 50-mL eggplant type flask. After the flask was purged with nitrogen, heating was started under a nitrogen flow. While stirring with a stirrer at normal pressure, temperature was raised from 170° C. to 200° C. A condensation reaction was effected while distilling off water thus generated. Low boiling point substances such as unreacted glycolic acid were distilled off by reducing the pressure to 40 mmHg by a vacuum pump and heating the reaction mixture at 200° C. for 2 hours. The prepolymer thus obtained was substantially colorless and transparent.

A depolymerization reaction was performed by elevating the temperature to 260° C. and the pressure reduction degree to from 3 to 5 mmHg. The distillate was collected in a cold trap with ice water. As a result of gas chromatographic analysis, no peak other than that of glycolide was observed. The residue in the flask was lightly colored, but the glycolide in the trap was almost colorless.

Then, the calcium glycolate slurry obtained in Comparative Example 1 was filtered through a funnel with a glass filter to obtain 32.4 g of wet crystals of calcium glycolate. A portion of the crystals were diluted with water to an adequate concentration. A glycolic acid concentration was analyzed using high performance liquid chromatography and an ammonia concentration was analyzed using ion chromatography. The resulting sample was used as a pre-washing sample. To the remaining portion of the wet crystals of calcium glycolate was added the same weight of distilled water heated to 50° C. After stirring with spatula, the resulting mixture was filtered through a funnel with a glass filter to obtain wet crystals of calcium glycolate (first washing). After a portion of the resulting crystals was analyzed in a similar manner to that of the pre-washing sample, it was washed and analyzed similarly (second washing). Further, third washing and analysis were performed similarly. The results are shown in Table 2.

TABLE 2

|  | Pre-washing | First washing | Second washing | Third washing |
|---|---|---|---|---|
| NH₃ Concentration [wt. %/GA] | 2.6 | 0.67 | 0.15 | 0.038 |
| GA collection percentage | 100% | 96.1% | 92.3% | 88.2% |

* GA collection percentage is that after each washing relative to 100%, that is, prewashing percentage Without interruption, a portion of the calcium glycolate slurry washed three times was subjected to sulfuric acid treatment as in Example 3 to obtain a 52.8 wt. % aqueous solution of glycolic acid. After purification steps by anion exchange and cation exchange, a purified aqueous solution of glycolic acid was collected. None of ammonium cations, calcium cations, glycine and iminodiacetic acid were detected from the collected solution.

Similar to Example 3, a portion of the resulting aqueous solution of glycolic acid was then charged in a 50-mL eggplant type flask. After the flask was purged with nitrogen, heating was started under a nitrogen flow. While stirring with a stirrer at normal pressure, the reaction mixture was heated at a temperature elevated from 170 to 200° C. A condensation reaction was effected while distilling off water thus generated. Low boiling point substances such as unreacted glycolic acid were distilled off by reducing the pressure to 40 mmHg by using a vacuum pump and heating the reaction mixture at 200° C. for 2 hours. The prepolymer thus obtained had a slight yellow color.

A depolymerization reaction was then performed by elevating the temperature to 260° C. and raising the pressure reduction degree to from 3 to 5 mmHg. The distillate was collected in a cold trap with ice water. As a result of gas chromatographic analysis, no peak other than that of glycolide was observed. The residue in the flask was colored brown and the glycolide in the trap was colored yellow.

Comparative Example 3

As Comparative Example, ammonia was removed by thermal hydrolysis of an α-hydroxy acid ammonium salt.

A 100-mL four-necked flask was charged with 50 g of a 52 wt. % aqueous solution of ammonium glycolate. The flask was equipped with, at the side tube thereof, a Liebig condenser having therebetween a distilling head fitted with a thermometer for measuring the temperature of an internal fluid and a thermometer for measuring a top temperature and, at the center, a three-one motor stirring blade. The whole system was dipped in an oil bath to raise the temperature of the internal liquid to the temperature shown in Table 3 and water and remove ammonia together with water. The final distillation amount was 23.3 g. Based on the analysis values at each time shown in Table 2, time-dependent changes of ammonia and glycoloamide were determined. The glycolic acid obtained finally was colored excessively and a highly viscous liquid. The treatment conditions are shown in Table 3 and measurement results of ammonia and glycoloamide concentrations are shown in FIG. 3.

TABLE 3

| Elapsed time [min] | Bath temperature [° C.] | Internal temperature [° C.] | Top temperature [° C.] |
|---|---|---|---|
| 0 | 110 | 21 | 21 |
| 18 | 115 | 95 | 21 |
| 24 | 115 | 102 | 26 |
| 30 | 120 | 104 | 39 |
| 35 | 120 | 105 | 40 |
| 39 | 125 | 108 | 98 |
| 46 | 125 | 109 | 100 |
| 53 | 130 | 110 | 100 |
| 63 | 130 | 111 | 100 |
| 71 | 130 | 112 | 100 |
| 81 | 130 | 113 | 100 |
| 93 | 130 | 114 | 100 |
| 107 | 135 | 116 | 100 |
| 117 | 135 | 118 | 100 |
| 127 | 135 | 120 | 100 |
| 134 | 140 | 123 | 100 |
| 142 | 140 | 126 | 100 |
| 159 | 145 | 130 | 100 |
| 188 | 145 | 136 | 100 |
| 209 | 145 | 144 | 100 |

Example 5

A 100-mL four-necked flask was charged with 50 g of a 40 wt. % aqueous solution of ammonium lactate. The flask was equipped with, at the side tube thereof, a thermometer and a reflux apparatus and, at the center, a three-one motor stirring blade. The whole system was dipped in a temperature-controlled water bath. The internal temperature was raised to 80° C. A 30 wt. % calcium hydroxide slurry (25.1 g) was added dropwise over 15 minutes. This means that 0.55 mol of calcium hydroxide was used per mol of ammonium lactate.

After treatment at 80° C. for 3 hours, the calcium lactate slurry thus obtained was sampled and diluted with distilled water to an adequate concentration. A lactate concentration and a lactic acid amide concentration were analyzed using high-performance liquid chromatography and an ammonia concentration was analyzed using ion chromatography. As a result, the ammonia concentration based on the weight of lactic acid was 0.027 [wt. %/lactic acid] and no lactic acid amide was detected.

Without interruption, a portion of the calcium lactate slurry thus obtained was filtered through a funnel with a glass filter as in Example 4. To the wet crystals of calcium lactate thus obtained was added the same weight of distilled water heated to 50° C. and the resulting mixture was stirred using a spatula, followed by filtration through a funnel with a glass filter. This operation was repeated three times. To a portion of the wet crystals of calcium lactate thus obtained, 50 wt. % sulfuric acid was added to give a molar ratio of 1.03 mol relative to 1 mol of calcium lactate while keeping its temperature at 60° C. The reaction mixture was saturated for one hour. The crystals of calcium sulfate thus obtained were filtered and separated through a funnel with a glass filter and a 52.2 wt. % aqueous solution of lactic acid was obtained as the filtrate. From the aqueous lactic acid solution, neither ammonia nor lactic acid amide was detected.

A portion of the resulting aqueous lactic acid solution was charged in a 50 mL eggplant type flask. After the flask was purged with nitrogen, heating was started under a nitrogen flow. While stirring with a stirrer at normal pressure, the reaction mixture was heated at a temperature elevated from 130 to 150° C. A condensation reaction was effected while distilling off water thus generated. Low boiling point substances such as unreacted lactic acid were distilled off by reducing the pressure to 40 mmHg with a vacuum pump and heating at 160° C. for 2 hours. The prepolymer thus obtained was substantially colorless and transparent. A depolymerization reaction was then performed by elevating the temperature to 220° C. and raising the pressure reduction degree to from 3 to 5 mmHg. The distillate was collected in a cold trap with ice water. As a result of gas chromatographic analysis, no peak other than that of lactide was observed. The residue in the flask was colored lightly, but the trapped lactide was almost colorless.

Figure 1:
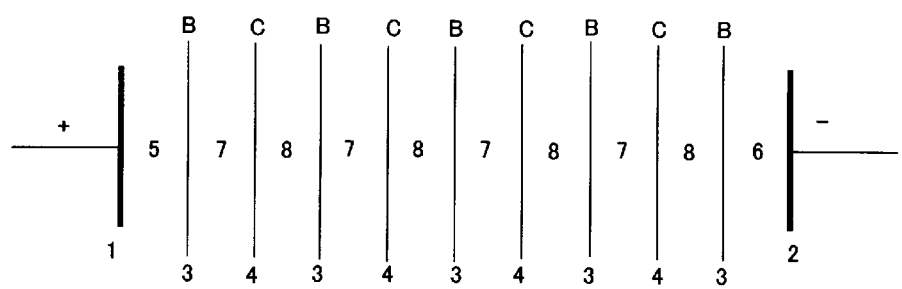
FIG. 1 is a schematic view of a two-compartment water decomposition electrodialyzer to be used in the present invention.
Figure 2:
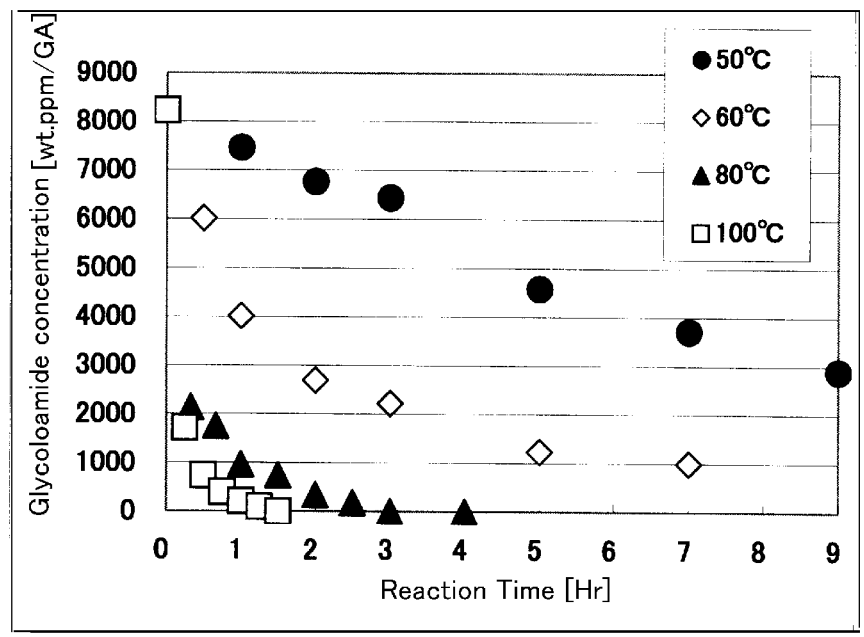
FIG. 2 shows a relationship between a reaction time of a reaction to obtain calcium glycolate by adding calcium hydroxide to ammonium glycolate and a concentration of glycoloamide.
Figure 3:
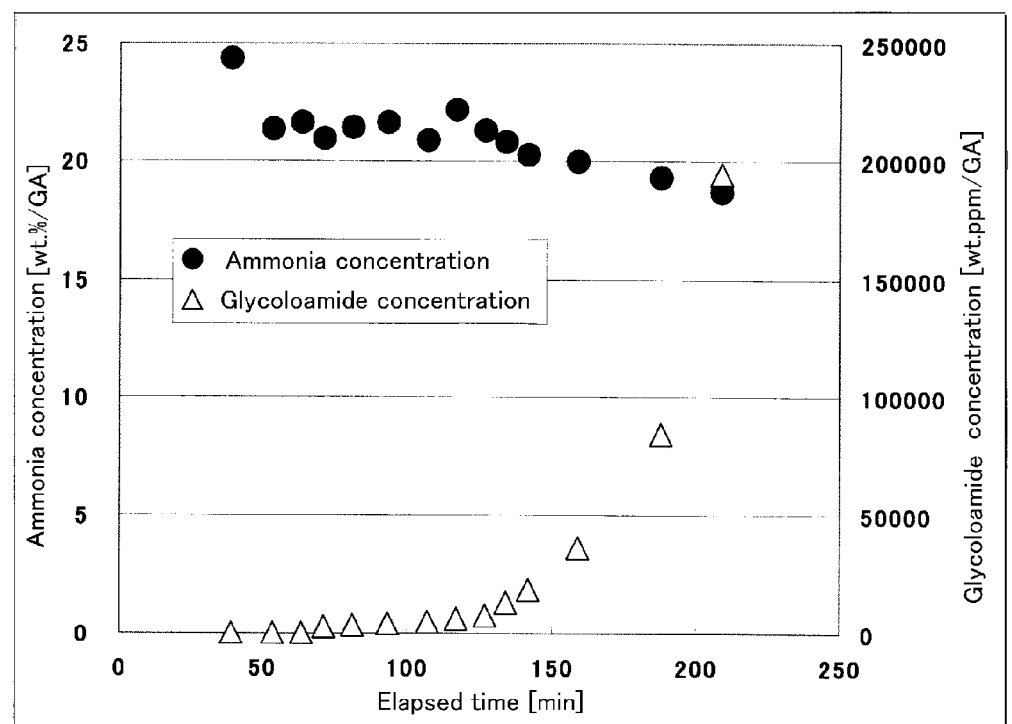
FIG. 3 illustrates a time-dependent change of ammonia and glycoloamide when ammonia is removed from ammonium glycolate in a conventional manner.

The invention claimed is:

1. A process for producing an α-hydroxy acid, which comprises:
   (1) a step of bringing a basic metal into contact with an aqueous solution of an α-hydroxy acid ammonium salt to produce an α-hydroxy acid metal salt while (i) controlling a concentration of an α-hydroxy acid amide residue in the solution to 500 [weight ppm/α-hydroxy acid] or less, and (ii) simultaneously removing ammonia generated in this step from the aqueous solution into a gas phase portion at a temperature exceeding 60° C., and
   (2) a step of desalting the α-hydroxy acid metal salt into the corresponding α-hydroxy acid.

2. The process for producing an α-hydroxy acid according to claim 1, wherein in Step (1), a concentration of an ammonia residue in the solution is controlled to 3 [weight %/α-hydroxy acid] or less.

3. The process for producing an α-hydroxy acid according to claim 1, wherein the aqueous solution of an α-hydroxy acid ammonium salt is obtained by a hydrolysis reaction of an α-hydroxynitrile.

4. The process for producing an α-hydroxy acid according to claim 3, wherein the hydrolysis reaction of an α-hydroxynitrile is an enzymatic catalytic reaction using nitrilase and/or combination of nitrile hydratase and amidase.

5. The process for producing an α-hydroxy acid according to claim 3, wherein the hydrolysis reaction of an α-hydroxynitrile is performed using nitrilase.

6. The process for producing an α-hydroxy acid according to claim 5, wherein the nitrilase is derived from genus *Acinetobacter*.

7. The process for producing an α-hydroxy acid according to claim 6, wherein the nitrilase is derived from *Acinetobacter* sp. AK226.

8. The process for producing an α-hydroxy acid according to claim 1, wherein the basic metal is at least one selected from the group consisting of hydroxides, oxides, and carbonates of an alkali metal, beryllium, or magnesium and in Step (2), the α-hydroxy acid metal salt is desalted by ion exchange.

9. The process for producing an α-hydroxy acid according to claim 8, wherein the basic metal is at least one selected from the group consisting of hydroxides, oxides, and carbonates of an alkali metal, beryllium, or magnesium and in Step (2), the α-hydroxy acid metal salt is desalted by electrodialysis.

10. The process for producing an α-hydroxy acid according to claim 1, wherein the basic metal is at least one selected from the group consisting of hydroxides, oxides, and carbonates of calcium, strontium, barium, or radium and in Step (2), the α-hydroxy acid metal salt is desalted by the addition of sulfuric acid.

11. The process for producing an α-hydroxy acid according to claim 10, wherein after Step (1), the α-hydroxy acid metal salt is collected in solid form by solid-liquid separation and then, washed and in Step (2), sulfuric acid is added to the α-hydroxy acid metal salt in solid form or a slurry obtained by adding water thereto.

12. The process for producing an α-hydroxy acid according to claim 10, wherein the basic metal is at least one selected from the group consisting of calcium hydroxide, calcium oxide, and calcium carbonate.

13. The process for producing an α-hydroxy acid according claim 1, which further comprises, after Step (2), a step of removing an impurity anion by using an anion exchange resin and a step of removing an impurity cation by using a cation exchange resin.

14. The process for producing an α-hydroxy acid according to claim 13, wherein the impurity cation contains a byproduct α-amino acid or iminodialkyl acid.

15. The process for producing an α-hydroxy acid according to claim 1, wherein the α-hydroxy acid is lactic acid or glycolic acid.

16. The process for producing an α-hydroxy acid according to claim 15, wherein the α-hydroxy acid is glycolic acid.

17. A process for producing a cyclic dimer ester comprising a step of synthesizing an α-hydroxy acid oligomer using, as a raw material, an aqueous solution of an α-hydroxy acid obtained by the process as described in claim 1 and a step of depolymerizing the α-hydroxy acid oligomer.

18. A process for producing a poly-α-hydroxy acid comprising a step of conducting a ring-opening polymerization reaction using, as a raw material, the cyclic dimer ester obtained by the process as described in claim 17.

19. The process for producing an α-hydroxy acid according to claim 1, wherein reaction time for Step (1) is at least 1.5 hour.

20. The process for producing an α-hydroxy acid according to claim 1, wherein an inert gas is introduced into the solution while the basic metal is added to the aqueous solution of an α-hydroxy acid ammonium salt.

21. The process for producing an α-hydroxy acid according to claim 20, wherein the inert gas comprises nitrogen gas and/or helium gas.

22. The process for producing an α-hydroxy acid according to claim 1, wherein the ammonia removed into the gas phase portion is collected.

23. A process for producing an α-hydroxy acid, which comprises:
   (1) a step of bringing a basic metal into contact with an aqueous solution of an α-hydroxy acid ammonium salt to produce an α-hydroxy acid metal salt while (i) controlling a concentration of an α-hydroxy acid amide residue in the solution to 500 [weight ppm/α-hydroxy acid] or less, and (ii) simultaneously introducing an inert gas into the solution, and
   (2) a step of desalting the α-hydroxy acid metal salt into the corresponding α-hydroxy acid.

* * * * *